United States Patent [19]

McHugh

[11] Patent Number: 4,588,744
[45] Date of Patent: May 13, 1986

[54] METHOD OF FORMING AN AQUEOUS SOLUTION OF 3-3-BIS(P-HYDROXYPHENYL)-PHTHALIDE

[76] Inventor: John E. McHugh, 11633 S. Hawthorne Blvd., Hawthorne, Calif. 90250

[21] Appl. No.: 228,987

[22] Filed: Jan. 27, 1981

Related U.S. Application Data

[63] Continuation-in-part of Ser. No. 943,811, Sep. 19, 1978, Pat. No. 4,256,763.

[51] Int. Cl.$^4$ ............... A61K 31/19; A61K 31/34
[52] U.S. Cl. ............................. 514/470; 514/568; 549/308; 562/406
[58] Field of Search ............... 424/285; 514/568, 470; 562/406; 549/308

[56] References Cited

U.S. PATENT DOCUMENTS

| | | | |
|---|---|---|---|
| 4,046,918 | 9/1977 | Cebrian | 424/338 |
| 4,046,919 | 9/1977 | Cebrian | 424/331 |
| 4,256,763 | 3/1981 | McHugh | 424/285 |

OTHER PUBLICATIONS

Chemical Abstracts, 76: 103763z (1972).
Handbook of Nonprescription Drugs, 5th ed., 1977, p. 42.
Remington's Pharm. Sciences, 11th ed., 1956, pp. 975–976.
Chemical Abstracts, 83: 84879t (Klein), 1975.

*Primary Examiner*—Leonard Schenkman
*Attorney, Agent, or Firm*—Lyon & Lyon

[57] ABSTRACT

There is disclosed a method and composition of matter for treating mammalian inflammatory viral infections, acne, dermatitis, and arthritic conditions comprising the application of 3,3-Bis(p-hydroxyphenyl)-phthalide (phenolphthalein) by itself, or in combination with a carrier, or in a mixture with a bicarbonate salt of Group I of the Periodic Table, or in combination with both a carrier and bicarbonate salt. These mixtures can be anhydrous or aqueous solutions and can be applied either by injection, ingestion, or topically.

1 Claim, No Drawings

METHOD OF FORMING AN AQUEOUS SOLUTION OF 3-3-BIS(P-HYDROXYPHENYL)-PHTHALIDE

CROSS-REFERENCES

This is a continuation-in-part of application Ser. No. 943,811, filed on Sept. 19, 1978 now U.S. Pat. No. 4,256,763.

BACKGROUND OF THE INVENTION

This invention relates to the discovery that 3,3-Bis (p-hydroxyphenyl)phthalide is an effective treatment for certain inflammatory skin conditions, especially those of a viral origin, arthritis, rheumatism, and rheumatoid arthritis.

Phenolphthalein has long been known as one of a group of primary diphenylmethane cathartics. The cathartic effect of phenolphthalein was reportedly discovered in 1902 and since that time it has been widely employed in laxative formulas. It is also reported that phenolphthalein is relatively non-toxic. Goodman & Gillman, *Pharmacological Basis of Therapeutics* (4 Ed. 1977) "Cathartic and Laxatives" pp. 1021 and 1022. Phenolphthalein is also used as an indicator in titrations of mineral and organic acids and most alkalies.

Although inflammatory viral infections may be caused in humans, mammals, and other animals by a wide variety of viruses, a common virus which produces persistently hard to treat conditions is the Herpes Simplex virus. In humans Type I normally produces above-waist infections while Type II produces lesions below the waist, in the genital region. Common manifestations of viral infection, including Herpes Simplex I infections are labialis (cold sores, fever blisters, etc.) pharyngitis, keratitis, skin infections (herpetic whitlow), encephalitis, and chronic ulcerative stomatitis. Herpes Simplex Type II may cause progenitalis oropharyngeal infections, meningitis and encephalitis. Other manifestations of inflammatory viral infections are canker sores, sun blisters and other such skin lesions and ulcerous conditions. In mammals, such as cows, bulls, and sheep, both Types I and II infect eyes, ears, mouth, and upper respiratory systems. Birds, such as parrots, are virally infected in their digestive tracts among other regions, by what is known as New Castle disease.

Inflammatory viral infections have proven very difficult to treat and in many instances are allowed to run their course with symptomatic treatment such as ointments, local anesthetics and the like. Treatment for Herpes Simplex infections includes dusting with bismuth formic iodide, application of camphor spirit, epinephrine, idoxuridine, adenine arabinoside, large doses of steroids and x-ray or grenz ray therapy.

Inflammatory skin conditions (dermatitis) which occur frequently include photodermatitis and actinic dermatitis such as sunburn, actinic keratosis and the like, eczema pruritus, acute and chronic lesions, burning, swelling and blistering. These conditions are also difficult to treat with moisturizing creams, lotions and other topical agents being employed.

Acne is a disease of the pilosebaceous unit which includes the hair follicle and its sebaceous gland. They are most numerous on the face but also are found in abundance on the back, chest and upper arms. (L. Kaminester, "Acne," *Journal of the American Medical Association*, May 19, 1978, Volume 239, No. 20, pages 2171–72). Normally the sebaceous glands secrete an oily material called sebum which rises to the top of the hair follicle and then flows out onto the skin surface. Acne occurs when the canals through which the oily sebum flows become plugged up. Bacteria, chiefly *Corynebacterium acnes*, live in the hair follicles and break down complex fats into triglycerides and free fatty acids.

The plugged hair follicle, or comedo, often ruptures into the lower skin areas and dumps free fatty acids, horn, fat, hair and bacterial products into the dermis, creating a toxic foreign body response which can cause scarring. Recently recommended treatment of acne includes oral antibiotics that effectively decrease the bacterial count of *C acnes*. These include tetracycline and erythromycin which selectively concentrate around the hair follicles, thus reducing the *C acnes* count and subsequent inflammation. Those antibiotics may also be applied in topical application. Kaminester reports that topical applications of antibiotics are inferior to orally administered antibiotics and should not be used in severe cases of inflammatory acne. Topical tretinoin and benzoyl peroxide preparations have also had beneficial effects.

Arthritis is the inflammation of a joint usually accompanied by pain. It can result from a number of conditions including infection, trauma, and degenerative joint diseases.

Rheumatism is an acute or chronic condition characterized by soreness and stiffness of muscles, and pain in joints and associated structures.

Rheumatoid arthritis is a systemic disease characterized by inflammatory changes in joints and related structures. It tends to be chronic. There is no specific cure for it and physical therapy and orthopedic measures are often utilized in its treatment. Various special methods of treatment have been tried with diverse degrees of effectiveness.

It is well known that phenolphthalein is highly insoluble in water. When phenolphthalein is ingested into the human body less than 15% of the active drug in solution is absorbed into the blood stream. The rest of the drug is excreted in the feces.

It is an object of this invention to provide a methodology for rendering phenolphthalein readily soluble in either hot or cold water. This solubility not only enhances its ingestibility by and injectability into the human organism or other mammals but also allows for topical applications using aqueous media, or the preparation of capsules or tablets for ingestion by the mammalian organism.

It is an object of the present invention to provide a fast acting, effective treatment of inflammatory viral infections and skin conditions.

It is a further object to provide a topical agent to arrest dermatitis conditions.

It is a further object of this invention to provide a fast, acting, effective treatment of arthritis, rheumatism, and rheumatoid arthritis, and its pain and symptoms.

It is yet a further object of the invention to provide a topical agent which helps prevent and aids in curing acne.

SUMMARY OF THE INVENTION

The method of the invention provides for the treatment of inflammatory viral infections, acne and arthritis, rheumatism, and rheumatoid arthritis, by the application of 3,3-Bis(p-hydroxyphenyl)-phthalide (hereafter phenolphthalein) by itself, or in combination with a carrier, or in a mixture with a bicarbonate salt of Group I of the periodic table. These mixtures can be anhydrous or solutions in water, and treatment can be by injection, ingestion, or topical application to the infected area. These mixtures can be prepared in tablet, capsule, or similar form for use by ingestion.

These mixtures can also be applied as a topical agent within the scope of the invention to relieve or cure Herpes Labialis, cold sores, sun blisters, canker sores, photodermatitis, actinic dermatitis, actinic keratosis and dermatitis manifested as pruritus, acute and chronic lesions, burning, swelling, and blistering. When applied as a topical agent phenolphthalein can be mixed with a suitable carrier and can be formulated to provide a moisturizing cream with anti-viral action. Alternatively, it can be mixed with a bicarbonate salt to form either an aqueous solution or anhydrous mixture.

In a topical preparation including antibiotics, phenolphthalein may be applied to effectively treat acne. In such applications the suitable carrier will be selected to avoid comedogenic agents.

DETAILED DESCRIPTION

In an informal clinical study 41 patients with symptoms of Herpes Labialis were treated with oral dosages of phenolphthalein. The patients were treated at different times over a period of about two months. The initial dosage was one hundred milligrams administered every 8 hours for the first day and every 12 hours thereafter. Due to complaints related to the laxative effect of the phenolphthalein, the dosage was reduced to 30 milligrams in the early stages of the testing. Of the 41 patients treated, 39 made complete recovery within two days without any noticeable development of the cold sore. The other two patients made complete recovery with no swelling or visible evidence of the cold sore remaining after three days. A control group of 24 patients with Herpes Labialis history were selected at random from clinical files as a control group. Of the 24 patients, 5 were excluded because of the total absence of early indications of infection. The other 19 patients were treated conventionally over a 10 day period. Only 4 experienced even partial relief from developing cold sores and 15 developed active cold sores and blisters which lasted up to 4 weeks.

Follow-up observations on the 41 patients treated with phenolphthalein disclosed no development of Herpes Labialis. The results of this informal study indicate that phenolphthalein is a very effective drug for preventing and arresting the development of cold sores and blisters at the time of initial appearance in patients.

Oral dosages of phenolphthalein have been successfully administered to victims of Herpes Simplex infections, including cold sores, fever blisters and Herpes Genitalis. Oral dosages have also proved effective to relieve and cure canker sores within a matter of hours.

Phenolphthalein has successfully been combined with agents to relieve other cold and flu symptoms often associated with inflammatory viral infections. Tablets were prepared for this purpose having the ingredients listed in Table 1. In some formulations the phenolphthalein content was one hundred milligrams but this amount was reduced to thirty milligrams because of complaints of the laxative effect. Other formulations comprising antihistamines, decongestants, analgesics and antipyretics will be readily apparent to those skilled in the art and may be selected for specific conditions to be treated.

TABLE I

| Ingredient | Nominal Amount | Analyzed Amount |
|---|---|---|
| Phenolphthalein | 30 mg. | 27.6 mg. |
| Acetaminophen | 325 mg. | 316.0 mg. |
| Caffeine | 33 mg. | 36.1 mg. |
| Chlorpheniramine Maleate | 2 mg. | 1.9 mg. |
| Phenylephrine HCl | 10 mg. | 9.7 mg. |

The inventor has been contacted by more than 20 men and women who indicated they were Herpes Simplex sufferers and that they received relief from cold sores and other Herpes Simplex inflammations by taking the tablets. The recommended dosage is one tablet every eight hours for the first day followed by one tablet every twelve hours until sypmtoms disappear. One person reported that she was a cold sore sufferer for years and that her ingestion of tablets, having either 30 or 100 milligrams of phenolphthalein with the remainder of the ingredients as set forth in Table 1, provided satisfactory results in combating cold sores.

A male who used tablets having the composition set forth in Table 1 reported that he had suffered from diagnosed Herpes Simplex II since 1972. He reported he took the recommended dosages and that the development of Herpes Simplex II was halted.

Phenolphthalein has also been prepared for topical application by formulating it at a concentration of 250 mg. per ounce with Natural Callagen Protein with pro-vitamin D-panthenol, lecithin and allantoin. The topical formulation provided a moisturizing cream which was effective in treating dermatitis conditions including photodermatitis, actinic dermatitis, actinic keratosis, eczema, pruritus, acute and chronic lesions, burning, swelling, blistering and acne.

Phenolphthalein was formulated at the same concentration in a topical ointment with benzoyl peroxide and calamine base and demonstrated to be effective in providing relief from acne vulgaris and acne conglobate.

In treating dermatitis conditions one formulation included 500 milligrams of phenolphthalein combined with 2 ounces of a moisturizing skin cream containing purified water (USP), Vitamin E, polyoxyethylene monostearate, glycerol monostearate, propylene glycol, ethyl alcohol, stearyl alcohol and parabens. That topical preparation was effective in promoting quick healing and growth of new skin in the treatment of rashes, blemishes and skin lesions commonly associated with old age.

As will be readily appreciated by those skilled in the art, phenolphthalein for oral application may be formulated with a variety of other agents to treat disease conditions associated with the disease for which phenolphthalein is selected. While orally administered phenolphthalein is effective in dosages at least up to 100 milligrams, the preferred dosage is from about 15–30 milligrams in order to avoid the objectionable laxative effect. The oral dosage may be administered in tablet, suspension or solution form.

In preparing topical applications for the treatment of external conditions, such as dermatitis and acne as well as arthritis, rheumatism, and related conditions, it is within the scope of the invention to formulate phenolphthalein with suitable carriers and bases to aid in the application to, or absorption into, the target or affected area. One group of carries is the oil-based carriers for external application this group includes dimethyl sulfoxide (DMSO), petrolatum, mineral oil, and anhydrous lanolin. In most topical applications the concentration of the phenolphthalein in the carrier may vary widely. For example 500 milligrams in 2 ounces of carrier is effective against acne. It is believed that a concentration of at least about 250 milligrams per ounce of carrier will be effective.

Another carrier useful in external application is the mixture of 10% methyl salicylate and lanolin, with 20% phenolphthalein. Triethanolamine salicylate can be substituted for methyl salicylate. A mixture of polyethylene glycol as a carrier with phenolphthalein is also effective in external applications.

For external eyedrop applications the mixture of 0.1% phenolphthalein with the carrier solution of 1.4% polyvinyl alcohol, and 0.004% benzalkonium chloride as a preservative, with sodium chloride and edetate disodium as maintainers of the isotonicity of the solution is useful. Another solution for external eyedrop application can be prepared with phenyl mercuric nitrate, benzalkonium chloride, and boric acid as the carrier solution, with phenolphthalein in an effective dosage amount. The above examples are not meant to be limiting, and the scope of the invention includes all effective concentrations of phenolphthalein in carriers.

Topical applications were prepared for the treatment of the external conditions, diseases and symptoms of arthritis, rheumatism, and rheumatoid arthritis or similar conditions. Phenolphthalein was formulated with a topical carrier of dimethyl sulfoxide (DMSO) to aid in the application of phenolphthalein to, and its abosrption into, the affected area for the relief of pain and the treatment of the area. It has been discovered that DMSO is an especially effective solvent for phenolphthalein. As little as one milliliter of liquid DMSO will dissolve two-hundred milligrams of phenolphthalein, or powders containing phenolphthalein. This factor coupled with the known ability of DMSO to penetrate organic tissue are believed to allow smaller dosages of phenolphthalein to be used in both oral and topical applications as well as in preparation of injectable solutions. For example the DMSO/phenolphthalein solution can be formulated into topical carriers which should enhance the penetration of phenolphthalein into the skin, or ingested.

In preparing the mixture of phenolphthalein and DMSO, one effective mixture is 150 milligrams phenolphthalein in 1 milliliter DMSO. This concentration is not viewed as a lower limit as the maximum solubility of phenolphthalein in DMSO has not been determined. Another effective mixture requires mixing DMSO with phenolphthalein (already in aqueous solution), and then the further combination of this resulting solution with any suitable base cream, ointment or other carrier, such as lanolin or petrolatum.

In order to provide for greater mammalian systemic activation, absorption, and circulation of the phenolphthalein at a strength greater than 15% of the dosage administered, penetration of the stomach and small intestinal walls for absorption into the blood stream is required. Since the human body and mammalian circulatory systems and body fluids are aqueous based, water solubility of phenolphthalein enhances its efficacy.

In preparing water soluble preparations for the treatment of all of the above conditions the following is within the scope of the invention. By preparation of a mixture of phenolphthalein and a bicarbonate salt the efficacy by absorption of phenolphthalein can be increased from the 15% of the dosage, noted above. While the actual increase has not been determined, in view of the subsequent examples, it is believed that phenolphthalein can be rendered virtually completely water soluble. Thus a greater amount of the dissolved phenolphthalein will pass through the intestinal walls in an oral application. This absorption will greatly enhance the ability of phenolphthalein to treat viral infections such as those of Herpes Simplex Types I and II. As stated above, the preferred dosage is between 15 and 30 milligrams of phenolphthalein in an oral application to avoid laxative effects. At a 15% maximum absorption, only approximately 2 to 5 milligrams would actually be absorbed in mammalian systems. However, with the exceptional increase of water solubility of this invention, virtually the entire dosage of phenolphthalein is believed able to pass through the intestinal walls. This allows the dosage size to be substantially decreased.

This aspect of the invention involves the mixing of phenolphthalein and sodium bicarbonate with water, the formation of a moist paste, the heating of this paste to a point less than the boiling point of water, the evaporation of substantially all the water in the paste thus forming a substantially anhydrous mixture, grinding this resultant mixture into a powder, dissolving this powdered mixture into water either hot or cold, utilizing stirring if necessary, whereby a solution of phenolphthalein is formed. The resultant solution can be applied to the afflicted human, mammal, or other animal, hypodermically, intramuscularly, intravenously, subcutaneously, topically, or by ingestion.

By way of example but in no way limiting on the scope of the claims or the invention are the following examples:

EXAMPLE I

Phenolphthalein (a N.F. purified grade of 3,3-Bis(p-hydroxyphenyl)-phthalide) and sodium bicarbonate ($NaHCO_3$), both in powdered form were mixed in the ratio of four parts by weight of the phenolphthalein with one part by weight of the bicarbonate. The powdered mixture was mixed thoroughly and then moistened lightly with distilled water to form a mixture with a paste consistency. Within a very short period of time, less than 5 minutes thereafter, this mixture was then heated to approximately 80° Centigrade for about 30 minutes. At the end of this period substantially all the moisture had evaporated. Thereafter the resulting mixture was crushed to a powder consistency. Then, 200 milligrams powder was completely dissolved in four ounces of hot water (in the range of 120° to 170° Fahrenheit) to form a solution. The resulting solution was ready for application either by injection, topically, or direct ingestion.

EXAMPLE II

The dry powder prepared according to Example I was dissolved in cold water while stirring. After about 5 minutes a stable solution was formed. The solution was ready for application by injection, topically, or by ingestion.

EXAMPLE III

After the formation of the dry powder according to Example I, the mixture can be made into tablets, or placed into gelatinous capsules for application by oral ingestion.

EXAMPLE IV

In carrying out the methods of Example I, the paste mixture was heated to approximately 93 degrees Centigrade. This shortened the time for evaporation of the water to less than 30 minutes.

EXAMPLE V

After mixing the powdered phenolphthalein and bicarbonate compounds as described in Example I, the resulting powdered mixture was mixed with hot water (between 120° and 170° Fahrenheit) by stirring, in a ratio of 200 milligrams of powder per four ounces of water. All of the phenolphthalein did not dissolve into the alkaline solution of sodium bicarbonate. Instead a suspension of phenolphthalein was formed. Within approximately three minutes, about 50% of the phenolphthalein settled out of solution.

EXAMPLE VI

Fifty (50) milligrams of sodium bicarbonate was placed in hot water with stirring until the sodium bicarbonate was dissolved. Thereafter, 200 milligrams of phenolphthalein was added to this solution and stirring took place for approximately 15 minutes. The phenolphthalein settled out of the solution very rapidly after stirring ceased. Approximately 50% of phenolphthalein settled out in less than about five minutes.

EXAMPLE VII

Phenolphthalein powder was moistened with water and thereafter heated and dehydrated. The product was a dry phenolphthalein powder. Sodium bicarbonate powder was moistened to paste consistency with water and heated to dryness. The sodium bicarbonate thus prepared was dissolved in hot water. The previously treated phenolphthalein was added to this solution. The phenolphthalein required approximately 10 to 15 minutes of stirring to form a suspension. Within 5 minutes after stirring ceased, the phenolphthalein started to settle out.

EXAMPLE VIII

The method of preparation of the mixture for treatment of antiviral infection as described in Example I was modified by changing the ratio of components to anywhere from one part phenolphthalein to one part sodium bicarbonate (a 1:1 ratio), to ten parts phenolphthalein to one part sodium bicarbonate (a 10:1 ratio). Each of these preparations was water soluble as described in Example I.

EXAMPLE IX

It was also found that the method of Example I could be modified by using a ratio of as little as 1 part of phenolphthalein to 2 parts sodium bicarbonate (1:2 ratio). There was no recorded detrimental effect on the solubility of phenolphthalein in water.

While specific formulations have been given above, it is not intended that they limit the scope of the invention. The invention is limited only by the scope of the appended claims set forth below.

What is claimed is:

1. The method of forming an aqueous solution of 3,3-Bis(p-hydroxyphenyl)-phthalide, suitable for treating mammals afflicted with the condition, disease, or symptom of inflammatory viral infection, cold sores, sun blisters, canker sores, actinic dermatitis, actinic keratosis, dermatitis, and acne comprising:

(a) making a mixture of 3,3-Bis(p-hydroxyphenyl)-phthalide and sodium bicarbonate;
(b) adding water to the mixture to yield a paste;
(c) heating the paste to less than the boiling point of water for a time sufficient to evaporate substantially all water, forming a substantially dry mixture; and
(d) dissolving the mixture in water.

* * * * *